United States Patent
Beudeker et al.

(10) Patent No.: US 10,453,360 B2
(45) Date of Patent: Oct. 22, 2019

(54) ULTRASOUND SIMULATION METHODS

(71) Applicants: VIRTAMED AG, Schlieren (CH); EIDGENOESSISCHE TECHNISCH HOCHSCHULE ZURICH (ETHZ), Zurich (CH)

(72) Inventors: Erika Beudeker, Schlieren (CH); Basil Fierz, Schlieren (CH); Sebastian Martin, Schwerzenbach (CH); Carolyn O'Brien, Schlieren (CH); Stefan Tuchschmid, Zurich (CH); Maxim Makhinya, Zurich (CH); Orcun Goksel, Zurich (CH)

(73) Assignee: VIRTAMED AG, Schlieren (CH)

( * ) Notice: Subject to any disclaimer, the term of this patent is extended or adjusted under 35 U.S.C. 154(b) by 10 days.

(21) Appl. No.: 15/768,204

(22) PCT Filed: Oct. 14, 2016

(86) PCT No.: PCT/EP2016/074707
§ 371 (c)(1),
(2) Date: Apr. 13, 2018

(87) PCT Pub. No.: WO2017/064249
PCT Pub. Date: Apr. 20, 2017

(65) Prior Publication Data
US 2018/0301063 A1     Oct. 18, 2018

Related U.S. Application Data

(60) Provisional application No. 62/242,322, filed on Oct. 16, 2015.

(51) Int. Cl.
G09B 23/28     (2006.01)
G09B 23/30     (2006.01)
(Continued)

(52) U.S. Cl.
CPC ............ *G09B 23/281* (2013.01); *A61B 8/145* (2013.01); *A61B 8/4254* (2013.01);
(Continued)

(58) Field of Classification Search
CPC ......... G06T 19/006; G06T 2207/10136; G06T 3/4007; G09B 23/281; G09B 23/286;
(Continued)

(56) References Cited

U.S. PATENT DOCUMENTS 8,992,230 B2     3/2015 Tuchschmid et al.
2006/0142657 A1     6/2006 Quaid et al.
(Continued)

FOREIGN PATENT DOCUMENTS

WO     WO2009/117419     9/2009

OTHER PUBLICATIONS

Luis T. Merce, et al., "Assessment of the ovarian volume, number and volume of follicles and ovarian vascularity by three-dimensional ultrasonography and power Doppler angiography on the HCG day to predict the outcome in IVF/ICSI cycles", Human Reproduction, vol. 21, No. 5, 2006, pp. 12118-1226 (Year: 2006).*
(Continued)

*Primary Examiner* — Jin Cheng Wang
(74) *Attorney, Agent, or Firm* — DLA Piper LLP (US)

(57) ABSTRACT

An ultrasound simulation method for rendering an ultrasound image of an anatomy model, comprises acquiring, with at least one model sensor, a position and/or orientation of the model; acquiring, with at least one probe replicate sensor, a position and/or orientation of an ultrasound imaging probe replicate, the ultrasound imaging probe replicate interacting with low friction with at least one anatomy model surface, the model surface being deformed by the pressure of the ultrasound imaging probe replicate; aligning a VR/AR model to the tracked position and orientation of the
(Continued)

anatomy model and the ultrasound imaging probe replicate; interpolating a 2D ultrasound slice by sampling through a standard reconstructed 3D ultrasound volume, as a function of the tracked position and orientation of the anatomy model and the ultrasound imaging probe replicate.

20 Claims, 10 Drawing Sheets

(51) Int. Cl.

| | |
|---|---|
| G09B 9/00 | (2006.01) |
| G06T 19/00 | (2011.01) |
| G06T 3/40 | (2006.01) |
| A61B 8/00 | (2006.01) |
| A61B 8/14 | (2006.01) |
| A61B 8/08 | (2006.01) |
| A61B 90/00 | (2016.01) |

(52) U.S. Cl.
CPC ............ *A61B 8/4444* (2013.01); *A61B 8/461* (2013.01); *A61B 8/483* (2013.01); *G06T 3/4007* (2013.01); *G06T 19/006* (2013.01); *G09B 9/00* (2013.01); *G09B 23/286* (2013.01); *G09B 23/30* (2013.01); *A61B 2090/378* (2016.02); *A61B 2090/3925* (2016.02); *G06T 2207/10136* (2013.01)

(58) Field of Classification Search
CPC ........ G09B 23/30; G09B 9/00; A61B 8/4254; A61B 2090/378; A61B 2090/3925; A61B 8/145; A61B 8/4444; A61B 8/461; A61B 8/483
USPC .......................................................... 345/633
See application file for complete search history.

(56) References Cited

U.S. PATENT DOCUMENTS

| | | |
|---|---|---|
| 2010/0152880 A1 | 6/2010 | Boyden et al. |
| 2010/0179428 A1 | 7/2010 | Pedersen et al. |
| 2010/0198068 A1* | 8/2010 | Rivaz ..................... A61B 8/483 600/443 |
| 2013/0189663 A1 | 7/2013 | Tuchschmid et al. |
| 2014/0071165 A1 | 3/2014 | Tuchschmid et al. |
| 2014/0277678 A1 | 9/2014 | Vesto |
| 2014/0277739 A1 | 9/2014 | Kornbluh et al. |
| 2014/0343416 A1 | 11/2014 | Panescu et al. |
| 2015/0154889 A1 | 1/2015 | Tuchschmid et al. |
| 2015/0154890 A1 | 6/2015 | Savitsky et al. |
| 2016/0220302 A1* | 8/2016 | Zarins ...................... A61F 6/20 |
| 2017/0110032 A1* | 4/2017 | O'Brien ................... G09B 9/00 |
| 2017/0181730 A1* | 6/2017 | Ardon ................... A61B 8/0866 |
| 2018/0110554 A1* | 4/2018 | Zarins ..................... A61N 7/022 |

OTHER PUBLICATIONS

Lucy Coyne, et al., "3D ultrasound in gynecology and reproductive medicine", Women's Health (2008), vol. 4, No. 5, pp. 501-516 (Year: 2008).*

Kresimir Petrinec, "Patient-Specific Interactive Ultrasound Image Simulation with Soft-Tissue Deformation", University of California, 122 Pages, (Jan. 1, 2013).

International Search Report Issued in Application No. PCT/EP2016/074707 dated Feb. 6, 2017.

Dror Aiger, et al., "Real-Time Ultrasound Imaging Simulation", Real-Time Imaging, vol. 4, pp. 263-274, (1998).

M. Weidenbach, "Augmented reality simulator for training in two-dimensional echocardiography", Computers and Biomedical Research, vol. 33, pp. 11-22, (2000).

Orcun Goksel, et al., "B-Mode Ultrasound Image Simulation in Deformable 3D Medium", IEEE Transactions on Medical Imaging, vol. 28, No. 11, 14 Pages, (Nov. 2009).

Orcun Goksel, et al., "Haptic Simulator for Prostate Brachytherapy with Simulated Needle and Probe Interaction", IEEE Transactions on Haptics, vol. 4, No. 3, 11 Pages, (May 2011).

Orcun Goksel, et al., "Prostate brachytherapy training with simulated ultrasound and fluoroscopy images", IEEE Trans Biomedical Engineering, vol. 60, No. 4, pp. 1002-1012, (Apr. 2013).

A.T. Popescu, et al., "3D printing bone models extracted from medical imaging data", IEEE International Conference on Automation, QUality and Testing, Robotics, 5 Pages, (May 2014).

U.S. Appl. No. 15/294,275.

* cited by examiner a)

b)

c)

d)

510
520
500

530 a)

b)

c)

a)

b)

c)

ULTRASOUND SIMULATION METHODS

INTRODUCTION

The present invention relates to computerized medical simulation in general, and more specifically to virtual reality and/or augmented reality simulation devices and systems for medical training purposes.

BACKGROUND

Virtual Reality/Augmented Reality Medical Simulation

Medical imaging has become more and more used for both diagnostic/examination and therapeutic purposes in a number of medical applications, such as endoscopy for surgery, or ultrasound imaging for various gynecology and/or obstetrics applications, for instance in the embryo transfer procedure for In Vitro Fertilization (IVF). These new techniques may require dedicated training for physicians and surgeons to master the indirect hand-eye coordination required by the imaging system as well as the manipulation of the imaging tools in addition to the conventional medical instruments and procedures for a diversity of patient anatomies as may be encountered in medical practice. Computerized medical procedure training simulators may enable the physicians and trainees to develop and improve their practice in a virtual reality environment before actually practicing in the operation room.

Advanced medical procedure simulators may be based on a virtual reality ("VR") and/or a mixed or augmented reality ("AR") simulation apparatus by which the physician can experiment a medical procedure scenario. The VR/AR system may compute and display a visual VR/AR model of anatomical structures in accordance with physician gestures and actions to provide various feedback, such as visual feedback. In a VR system, an entire image may be simulated for display to a user, and in an AR system, a simulated image may be overlaid or otherwise incorporated with an actual image for display to a user. Various patient models with different pathologies can be selected. Therefore, natural variations as encountered over the years by practicing doctors can be simulated for a user over a compressed period of time for training purposes. The medical simulation procedure can be recorded and rehearsed for evaluation purpose. The VR/AR simulation system can also compute and provide various metrics and statistics.

VR/AR simulation systems such as the one described in U.S. Pat. No. 8,992,230 include a human anatomy model of a joint of organ in real size. The VR/AR simulation system may further comprise a medical instrument to more realistically simulate the medical procedure. The model is further adapted with sensors for tracking the position and/or orientation of both the anatomy model and the medical instrument. As described in U.S. Pat. No. 8,992,230, calibration units may be further used to automatically setup and align the VR/AR simulation system to a diversity of anatomy models and medical procedure training scenarios without requiring a cumbersome, manual calibration procedure each time a new model is adapted to the system.

A passive feedback VR/AR simulation system such as for instance the one described in U.S. Pat. No. 8,992,230 may also be used with a diversity of medical procedure training scenarios, some of which may possibly result in a mismatch between an anatomy model surface as touched by the trainee and a virtual environment surface as computed by the VR/AR simulation system and rendered on the screen. In order to further improve the passive haptic experience and increase the realism in such medical training scenarios, the VR/AR simulation system may be further adapted with space warping methods and systems as described in US patent application US20140071165.

Ultrasound Imaging Simulation

Most prior art ultrasound simulation solutions have been developed based on interpolative ultrasound simulation, as used for instance by a number of commercial ultrasound training simulators such as Medsim (http://www.medsim.com/), EchoCom (http://www.echocom.de) and MedCom/Sonofit (http://www.sonofit.de). These prior art simulators use a set of collected 2D images for each case, which are reconstructed into 3D volumes per case in an offline "case generation" stage with minor differences between individual methods in how the 3D volumes and their corresponding graphical models are generated. For instance, Dror Aiger and Daniel Cohen-Or described the use of deformable registration techniques for generating large 3D volumes from smaller swept scans in "Real-time ultrasound imaging simulation", *Real-Time Imaging*, 4(4):263-274, 1998. In "Augmented reality simulator for training in two-dimensional echocardiography", *Computers and Biomedical Research*, 33:11-22, 2000, M. Weidenbach, C. Wick, S. Pieper, K. J. Quast, T. Fox, G. Grunst, and D. A. Redel proposed to register the recorded patient-specific volumes to a generic 3D anatomical heart model, which they thus call augmented training. All the above methods present the user a non-deformable model of the anatomy. In other words, although the images may change with the transducer position/orientation in some simulators, they do not change according to the trainee's interaction with the mannequin or the virtual model, which negatively impacts the simulation realism.

Deformable Interactive Ultrasound Simulation

Compared to non deformable solutions, deformable, interactive ultrasound simulation may generate a better sense of simulator realism and consequent trainee immersion. In "B-mode ultrasound image simulation in deformable 3-D medium", *IEEE Trans Medical Imaging*, 28(11): 1657-69, November 2009, O. Goksel and S. E. Salcudean introduced the first interpolative simulator that allows for deformation by using a fast mapping technique for image pixels to be simulated, from the deformed simulation tissue coordinates to a nominal recorded volumetric coordinate frame. This method combines an input (reconstructed) 3D volume and interactive, volumetric tissue deformation models such as the finite element method and has been further applied to prostate brachytherapy simulation as published in Orcun Goksel, Kirill Sapchuk, and Septimiu E. Salcudean, "Haptic simulator for prostate brachytherapy with simulated needle and probe interaction", *IEEE Trans Haptics*, 4(3): 188-198, May 2011. It has also been applied to a transrectal ultrasound training application with fluoroscopy imaging as published in Orcun Goksel, Kirill Sapchuk, William James Morris, and Septimiu E. Salcudean, "Prostate brachytherapy training with simulated ultrasound and fluoroscopy images", *IEEE Trans Biomedical Engineering*, 60(4):n2002-12, April 2013.

However, the latter methods by Goksel et al. only used a virtual patient model for simplicity. In a passive haptic VR/AR medical simulator, a physical anatomy model (mannequin) is further used with medical tools or instruments to simulate the medical procedure training as realistically as possible. For example in a state of the art embryo transfer IVF medical procedure as represented by FIG. 1, tools such as an ultrasound probe 130, a speculum 120, and an embryo transfer catheter 112 may be used. As described for instance by http://www.advancedfertilitycom/ivf-embryo-transfer-catheter.htm, a stiffer outer sheath (catheter guide) is first used to guide the soft and flexible inner embryo transfer catheter 112 through the cervical canal to the proper location in the uterine cavity 100. Once at the right location, the transfer catheter 112 is loaded with the embryos 115 which are propulsed with the embryo transfer syringe 110 into the uterine cavity 100. The whole procedure requires very careful gesture as any misposition or wound to the uterine may result in the failure of the IVF, which is a very costly and time-consuming procedure for the patients. The IVF embryo transfer procedure is conducted under ultrasound imaging supervision, by means of an abdominal ultrasound probe 130. The user manipulates the abdominal ultrasound transducer 130 by pressing it on the belly skin and positioning and orienting it to optimize the ultrasound imaging capture. An ultrasound gel or jelly is used to facilitate the ultrasound propagation as well as the manipulation of the ultrasound transducer in contact with the patient skin. In general, a moderately full bladder 140 is advisable for better ultrasound imaging quality, which will more or less deform with the probe compression on the above patient skin. The speculum tool 120 is usually made of metal and thus acts as a shield to the ultrasound waves, which also results in specific artefacts into the ultrasound images.

As known to those skilled in the art, the simulation of such a complex ultrasound procedure may raise specific issues to ensure a realistic virtual-physical dualism, e.g. the image should appear only when the ultrasound probe physically touches the anatomy model also emanating only from the curved surface of contact. Deformation of the ultrasound images and its components such as the skin (high compression), the bladder (moderate compression) and the uterine, the speculum and the catheter (no compression) needs to be synchronized with the user manipulation of the ultrasound probe, so the latter interaction remains as realistic as possible.

In "Patient-Specific Interactive Ultrasound Image Simulation with Soft-Tissue Deformation", PhD thesis, University of California Los Angeles, 2013, K. Petrinec proposed to adapt a commercially available ultrasound simulator (www.sonosim.com) to further simulate the deformation of soft tissues when in contact with the ultrasound probe, based on the Goksel method. In this simulator, only 3-DOF motion trackers are used to track the ultrasound probe orientation—that is, the probe is assumed to be positioned at a given 3D static position over a mannequin, and the system does not track its translational movement.

More recently, as described in US20150154890, Sonosim further introduced a 5-DOF tracking solution for this simulator by adding a translation sensor as a patch that can be applied over a live body or an anatomy model, in association with an electronic tag, so that the probe translation over a curved surface may be further tracked. From a passive haptic perspective, one major drawback of this solution is the lack of realism when manipulating the probe compared to a real ultrasound procedure, as no ultrasound gel can be used with this probe according to its instructions of use (http://sonosim.com/support/). In particular, friction of the rigid plastic virtual probe tip over the anatomy model surface significantly increases when the user has to push the probe to compress the skin and get a better ultrasound image. This friction is much lower in a real procedure where ultrasound gel or jelly is used to improve the ultrasound capture, but in general, it is not desirable to use any liquid or gel in a training setup due to the overhead required to clean it.

There is therefore a need for better ultrasound simulation devices, methods and systems that facilitate a diversity of ultrasound training procedures without requiring an expensive hardware setup and cumbersome registration and calibration procedures.

BRIEF SUMMARY

It is an object of the present disclosure to provide an ultrasound simulation method for rendering on a display an ultrasound image of an anatomy model, the method comprising:
  acquiring, with at least one anatomy model sensor, a position and/or orientation of an anatomy model;
  acquiring, with at least one probe replicate sensor, a position and/or orientation of an ultrasound imaging probe replicate, the ultrasound imaging probe replicate interacting with low friction with at least one anatomy model surface, the anatomy model being deformed by the ultrasound imaging probe replicate pressure against the anatomy model surface;
  aligning a VR/AR model to the tracked position and orientation of the anatomy model and the ultrasound imaging probe replicate;
  interpolating a 2D ultrasound slice by sampling through a standard reconstructed 3D ultrasound volume, as a function of the tracked position and orientation of the anatomy model and the ultrasound imaging probe replicate.

Interpolating the 2D ultrasound slice may further comprise measuring a deformation depth as the distance between the ultrasound probe replicate surface position and the initial anatomy model surface position before anatomy model surface deformation and interpolating a 2D ultrasound slice by sampling through a standard reconstructed 3D ultrasound volume, as a function of the deformation depth. Interpolating the 2D ultrasound slice may also further comprise identifying at least one anatomy element to be sampled through a standard reconstructed 3D ultrasound volume, identifying a deformation property for the anatomy element, and interpolating the anatomy element area in the 2D ultrasound slice by sampling through a standard reconstructed 3D ultrasound volume, as a function of the deformation depth and the anatomy element deformation property.

The ultrasound simulation method may further comprise the steps of calculating an ultrasound simulation image for additional VR/AR model elements not represented in the reconstructed 3D ultrasound volume, as a function of the tracked position and orientation of the anatomy model and the tool; blending the 2D ultrasound slice and the ultrasound simulation image into a blended ultrasound image; and rendering the blended ultrasound image onto a display. The ultrasound simulation method may also comprise the steps of calculating a fading of a simulated ultrasound image as a function of the tracked position and orientation of the anatomy model and the probe replicate and rendering the faded simulated ultrasound image onto a display.

DETAILED DESCRIPTION

Figure 1:
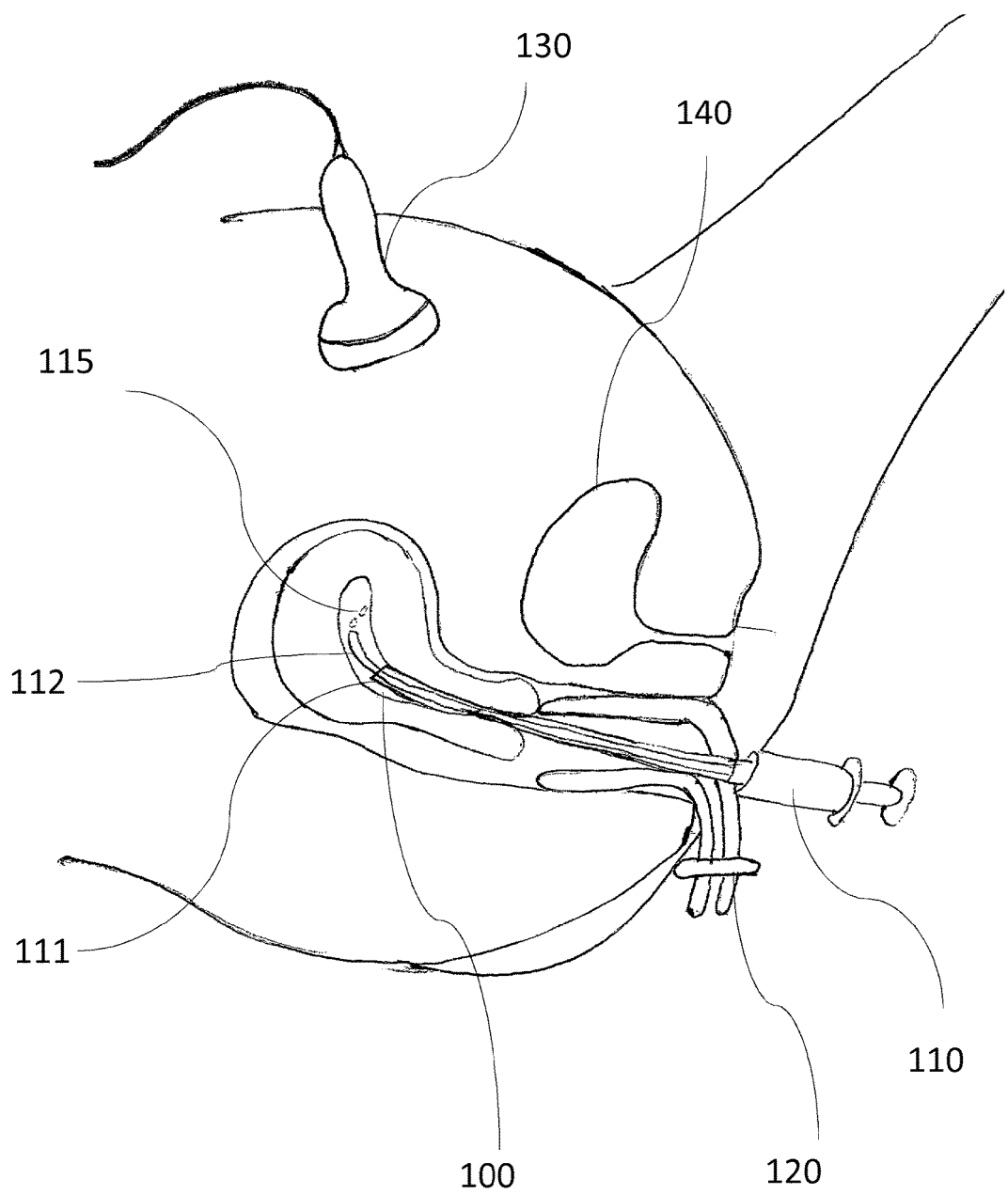
FIG. 1 illustrates an IVF embryo transfer procedure as known in the prior art.
Figure 2:
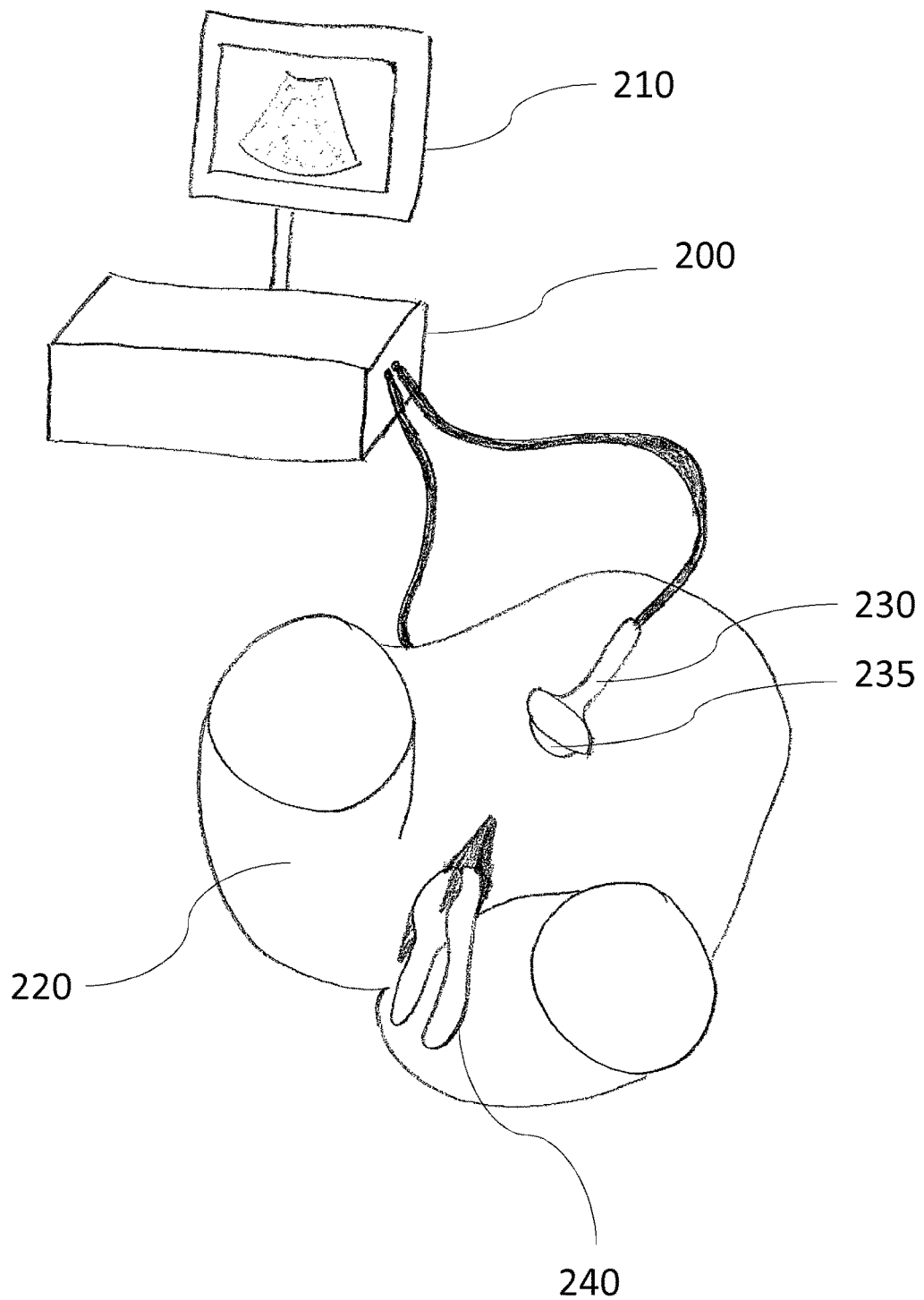
FIG. 2 illustrates an ultrasound simulator adapted to simulate an IVF embryo transfer procedure.

Embodiments of flexible ultrasound simulation devices, methods, and systems will now be described in more detail with reference to an exemplary medical simulation of an IVF embryo transfer procedure, as illustrated on FIG. 1. FIG. 2 shows a partial view of an ultrasound simulator system comprising a data processing unit 200, a display screen 210, and an anatomy model 220, according to an embodiment of the invention. For the purpose of illustration, in FIG. 2, a pelvic model 220 of the human female anatomy is shown, but other models can be used as well. Examples of models can be found in the catalogues of specialized anatomic model suppliers such as Limbs&Things, Bristol, UK. Some models may be representative of the human anatomy. Other models may be representative of an animal anatomy, e.g. for veterinary training purpose.

The anatomy model 220 may be made of plastic or any other suitable material. Preferably, the anatomy model 220 is made of a flexible material, such as flexible plastic, so that it can deform under pressure.

Figure 3:
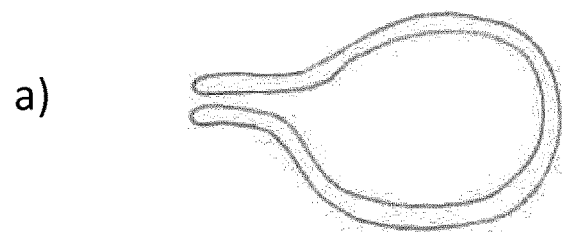
FIG. 3 shows four cervix and uterine anatomy models corresponding to some anatomy shapes that may be encountered in IVF embryo transfer medical practice.
Figure 3:
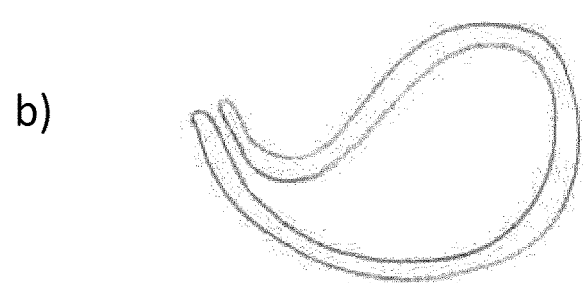
Figure 3:
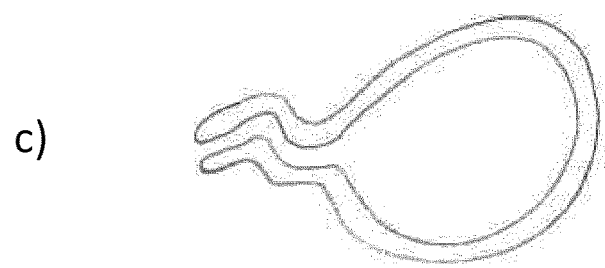
Figure 3:
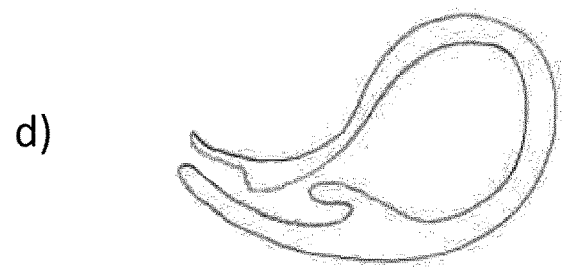

In some embodiments, the anatomy model 220, or parts of the anatomy model, may be interchanged with another similar anatomy model corresponding to different simulated patient characteristics or pathologies. For instance in an IVF embryo transfer training simulator, various combinations of cervix canal models (straight, tortuous, with a trap . . . ) and uterus types (axial, anteverted, retroverted . . . ) may be used to simulate more or less challenging variations of the patient pelvic organs anatomy. FIG. 3 shows four different cervix models: a) base cervix case with axial uterus, b) cervix entrance deflected down 40 degrees in an anteverted uterus, c) tortuous S-shaped cervix with axial uterus and d) trap cervix with 20 degrees anteverted uterus.

In some embodiments, the anatomy model 220, or parts of the anatomy model, such as for instance the cervix canal and/or the uterine in an OB/GYN training application, may be manufactured in the training room by using a manufacturing unit. Examples of such manufacturing units are well known to those skilled in the art of rapid prototyping; they may be based on additive manufacturing, such as 3D printing, or subtractive manufacturing, such as CNC milling.

In some embodiments, the anatomy model may also be manufactured according to a specific patient anatomy. Examples of manufacturing units as used in emerging medical applications are described for instance in Popescu, A. T.; Stan, O.; Miclea, L., "3D printing bone models extracted from medical imaging data", 2014 *IEEE International Conference on Automation, Quality and Testing, Robotics*, vol., no., pp. 1, 5, 22-24 May 2014. Patient specific anatomy models may also comprise specific patient pathologies. Patient specific anatomy models may be manufactured and interchanged with the anatomy model 220. Patient specific anatomy models may enable the physicians and trainees to develop and improve their practice in a virtual reality environment before actually performing the medical procedure. Furthermore, in order to support other medical procedures with ultrasound imaging, patient specific anatomy models may be interchanged with the anatomy model 220, such as for instance a bladder, a womb, an upper torso, a lower torso, or a joint model. In some embodiments the patient specific model may comprise parts of the anatomy model 220. The patient specific model may be manufactured by the manufacturing unit. In some embodiments the patient specific model may be created with additive manufacturing, such as 3D printing, or subtractive manufacturing, such as CNC milling.

The data processing unit 200 may comprise one or more central processing units ("CPU"), memory modules, controlling modules, and/or communication modules, for example. Other embodiments may include data processing units 200 with other configurations and combinations of hardware and software elements. A distributed data processing unit may be used. In some embodiments, a communication module of the data processing 200 may be connected to a manufacturing unit. In some embodiments, the data processing unit and the manufacturing unit may be combined in a single unit. Some or all of the data processing unit 200 components may be used to compute and display onto a display screen 210 a VR/AR simulation model that may correspond to a chosen medical procedure training scenario. Multiple display screens may also be used. The display screen 210 may comprise a touch interface to provide an interface for a physician during a simulation exercise. In other embodiments (not illustrated) the simulator cart may further comprise a camera.

In FIG. 2, the anatomy model 220 may comprise at least one position and orientation sensor (not represented). As described in U.S. Pat. No. 8,992,230, said position and orientation sensor may be associated with at least one calibration unit. For example, six degree of freedom ("6DOF") miniaturized magnetic tracking sensors may be used. Other embodiments are also possible, e.g. optical tracking or motion tracking may be used. The anatomy model 220 may be connected to the data processing unit 200 through a connection such as a USB link, other standard wired or wireless connection, or other communication link. The data processing unit 200 may receive the sensor information from the anatomy model 220 and may calculate the virtual anatomy model 220 position and orientation in accordance with the sensor measurement. The data processing unit 200 may use the calculated model 220 position and orientation to generate a visual model and display the visual model onto the display screen 210. As described in U.S. Pat. No. 8,992,230, the data processing unit 200 may compute the VR/AR model position and orientation by combining the absolute sensor measurement received from at least one anatomy model sensor with the pre-computed calibration data from the calibration unit associated with said sensor for the simulated VR/AR model.

As known to those skilled in the art, the VR/AR model may be aligned in 3D with the anatomy model based on assumptions on the anatomy model actual position and/or orientation. An anatomy model sensor may be attached to the anatomy model so that an absolute position and orientation of the VR/AR model matching the anatomy model in 3D space can be derived by the VR/AR simulator.

Medical imaging VR/AR simulators, such as endoscopy simulators, arthroscopy simulators and ultrasound imaging simulators, may further comprise an imaging probe replicate which is manipulated by the trainee while interacting with the anatomy model in real-time. An imaging probe replicate sensor may be attached to the probe replicate so that the position and/or orientation of the imaging probe may be derived by the VR/AR simulator. The VR/AR simulator may accordingly interpolate an image of the VR/AR model to be rendered on the VR/AR simulator screen, depending on both the acquired anatomy model sensor position and/or orientation and the acquired imaging probe sensor position and/or orientation, the latter imaging probe position and/or orientation defining the depth and field of view relative to the anatomy model.

FIG. 2 further shows a replicate of an ultrasound probe 230 which may be used to simulate an ultrasound imaging capture. For the purpose of illustration, in the case of IVF embryo transfer simulation, the ultrasound probe replicate 230 of FIG. 2 replicates the shape of a convex abdominal ultrasound transducer. Other probes may be replicated in other ultrasound training procedures, for instance a transvaginal or a transrectal probe for internal ultrasound examination. The replicate may not need to be an exact replicate of an ultrasound probe, but it may give a realistic haptic feedback similar to a real probe. The ultrasound probe replicate 230 may be handled and put in contact with the anatomy model surface by the trainee. The trainee may also push the anatomy model 220 surface with the ultrasound probe replicate 230 as in a real imaging procedure, and the anatomy model 220 surface may deform accordingly. The ultrasound probe replicate 230 may be adapted to comprise at least one position and orientation sensor, possibly in association with a calibration unit, for instance as described in U.S. Pat. No. 8,992,230. The data processing unit 200 may receive the sensor information from the ultrasound probe replicate 230 and may calculate the VR/AR model position and orientation in accordance with the model sensor measurement and the probe replicate sensor measurement respectively.

FIG. 2 further shows a medical tool 240 appended to the anatomy model 220. For the purpose of illustration, in the case of IVF embryo transfer simulation, the medical tool 240 of FIG. 2 is a speculum that can be inserted into the pelvic model 220 through the vulva portal of anatomy model. Other tools may be used, for instance an embryo transfer catheter, an embryo transfer syringe, a tenaculum, a Hegra dilator . . . . . . The medical tool 240 may be a standard medical tool suitable for various medical procedures, for instance a tenaculum tool that may be used in gynecology or in surgery. In some embodiments, the tool may be adapted to comprise at least one position and orientation sensor and one calibration unit associated with the position and orientation sensor, for instance as described in U.S. Pat. No. 8,992,230. In other embodiments, the position and orientation of the tool may be derived from the position and orientation of another element in the simulator system, such as an internal element to which the tool is mechanically bound without any remaining degree of freedom; for instance the tenaculum for steadying the cervix and uterus during the insertion of an intrauterine device is typically bound to the cervix position and orientation once steadying it. Thus, in some embodiments of the simulator system, a part of the anatomy model, for instance the cervix, rather than the tool, for instance the tenaculum, may be adapted to comprise at least one position and orientation sensor and one calibration unit associated with the position and orientation sensor, for instance as described for the femur or tibia parts in U.S. Pat. No. 8,992,230. Other embodiments are also possible to adapt the VR/AR ultrasound simulator to various medical practices, anatomy models, and tools.

The data processing unit 200 may receive the sensor information from the anatomy model 220, the probe replicate 230, and the tool 240 respectively. The data processing unit 200 may thus calculate the VR/AR model position and orientation in accordance with the anatomy model sensor measurement, the probe replicate sensor measurement, and the tool sensor measurement respectively.

Figure 4:
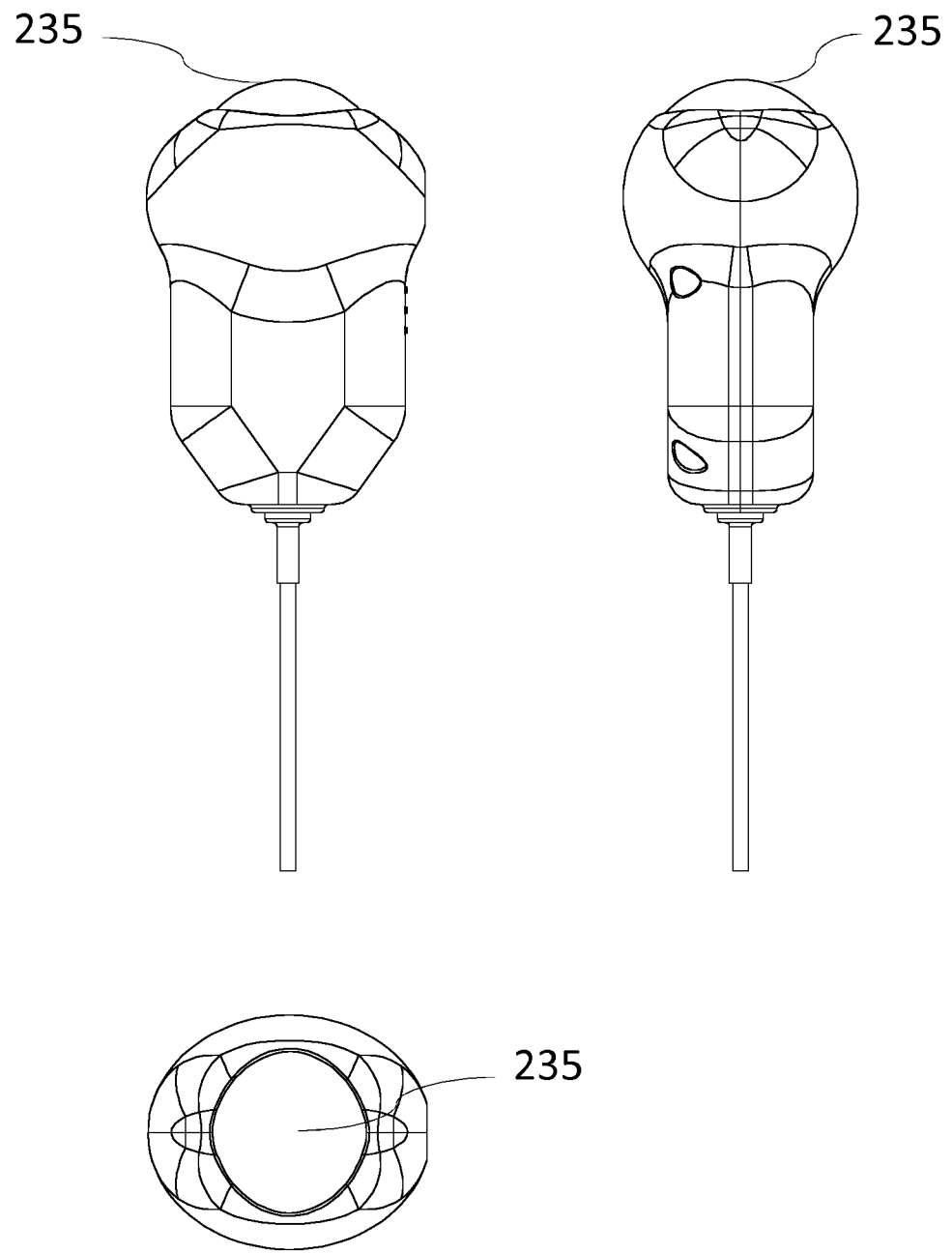
FIG. 4 shows engineering views of an exemplary ultrasound simulation probe adapted to provide realistic passive haptic feedback without requiring the use of ultrasound gel over the anatomy model.

In a possible embodiment, the tip of the ultrasound probe replicate 230 may be mechanically adapted to comprise a rolling part 235, such as a roller ball, which may simulate a more realistic low friction motion, when the ultrasound probe replicate 230 tip interacts with the anatomy model 220 surface. FIG. 4 shows the engineering views of a possible mechanical embodiment of a roller ball 235 which decreases the friction for different translational and rotational movements of the ultrasound probe replicate 230 over the anatomy model 220 surface. Other embodiments than a roller ball are also possible, for instance a low friction material may be used at the tip 235 of the ultrasound probe replicate 230, or on the anatomy model 220 surface.

The data processing unit 200 may use the calculated VR/AR model position and orientation to generate a visual model and display the visual model onto the display screen 210. As known to those skilled in the art, initial alignment of the VR/AR model with the position and orientation of the anatomy model 220, the ultrasound probe replicate 230 or the medical tool 240 may also require calibration. The methods and systems as described in U.S. Pat. No. 8,992, 230 for an endoscopy simulation system may be used to calibrate the VR/AR ultrasound simulation system.

In an ultrasound simulation system, the ultrasound image also needs to be rendered as realistically as possible. The data processing unit 200 may use the calculated VR/AR model position and orientation to identify a slice to be rendered from a reconstructed 3D ultrasound volume or a 3D ultrasound generation model and to render the simulated ultrasound image in real time onto the display screen 210.

Figure 5:
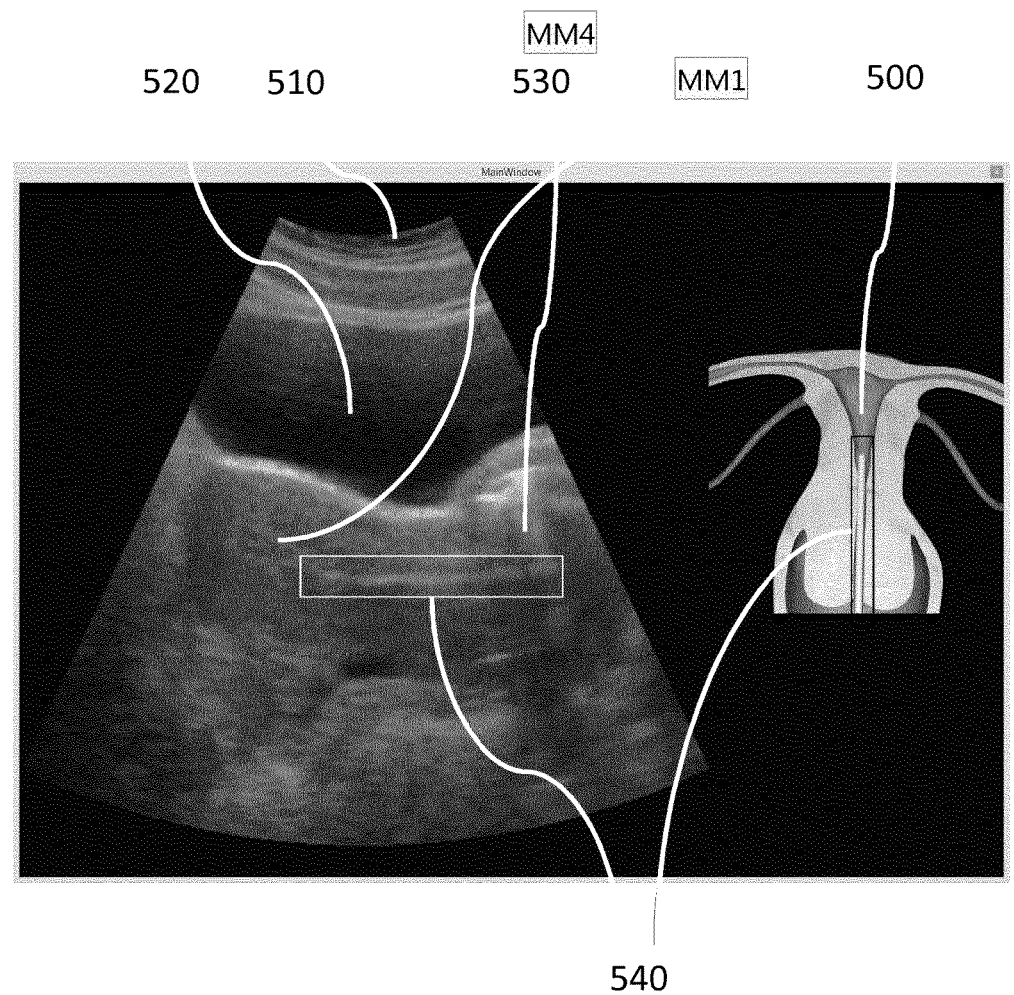
FIG. 5 shows a first screen capture of an ultrasound simulation rendering for the IVF embryo transfer procedure training.

FIG. 5 shows a screen capture of the ultrasound image and the VR/AR model as rendered on display screen 210 by the data processing unit 200 in the embryo transfer procedure. The embryo transfer catheter tool 540 is rendered into the uterine cavity 500 on the ultrasound image on the left as well as on the VR/AR model computer graphics representation on the right. A moderately filled bladder 520 and abdominal skin layers 510 are also visible in the ultrasound image as in a real ultrasound capture.

Figure 6:
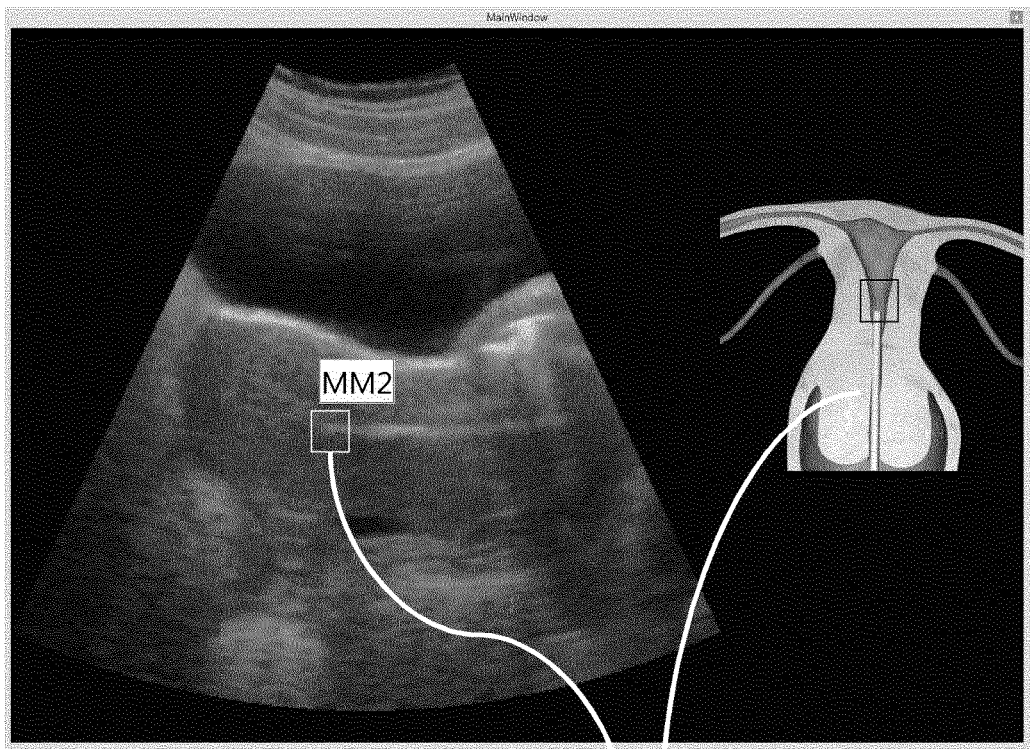
FIG. 6 shows a second screen capture of an ultrasound simulation rendering for the IVF embryo transfer procedure training.

FIG. 6 shows a screen capture of the ultrasound image and the VR/AR model as rendered on display screen 210 by the data processing unit 200 at the next step in the embryo transfer procedure, where the trainee transfers the embryos 600 from the embryo transfer catheter into the uterine cavity.

In a possible embodiment, the data processing unit 200 may be adapted to implement the interpolative ultrasound simulation methods as proposed by Goksel et al. to render realistic ultrasound images by interpolating a 2D slice in a 3D ultrasound volume reconstructed from formerly registered ultrasound image records, such as MR or CT data records, in combination with real-time induced deformations due to the user interaction with the ultrasound simulator system. Other methods may be used, for instance the ultrasound simulation may use a ray-based generated ultrasound simulation with segmentation rather that interpolative ultrasound simulation methods, as known to those skilled in the art of ultrasound simulation. A diversity of different patient VR/AR models may also be used as the basis for a diversity of ultrasound practice training scenarios, for instance to represent different pathologies. In order to further improve the passive haptic experience and increase the realism in such diversity of medical training scenarios without requiring too many different setups of the underlying anatomy model, the VR/AR ultrasound simulation system and methods may be further adapted with space warping methods and systems as described in US patent application US20140071165.

As will be apparent to those skilled in the art, the low friction interaction between the probe replicate 230 and the anatomy model 220 surface raises specific challenges for a realistic imaging rendering method compared to prior art simulator setups. Indeed, when the user manipulates the probe replicate 230 with low friction interaction with the anatomy model 220 surface, a broad area may be covered by the probe replicate, possibly out of the recorded ultrasound volume images. In particular the anatomy model 220 surface may be deformed as realistically as in real examination, resulting in different levels of abdominal compression by the simulated probe 230 and different resulting images needs to be simulated accordingly, as realistically as possible. It is no longer possible to rely upon a fairly static position of the imaging capture position and orientation the proposed simulator system.

Figure 7:
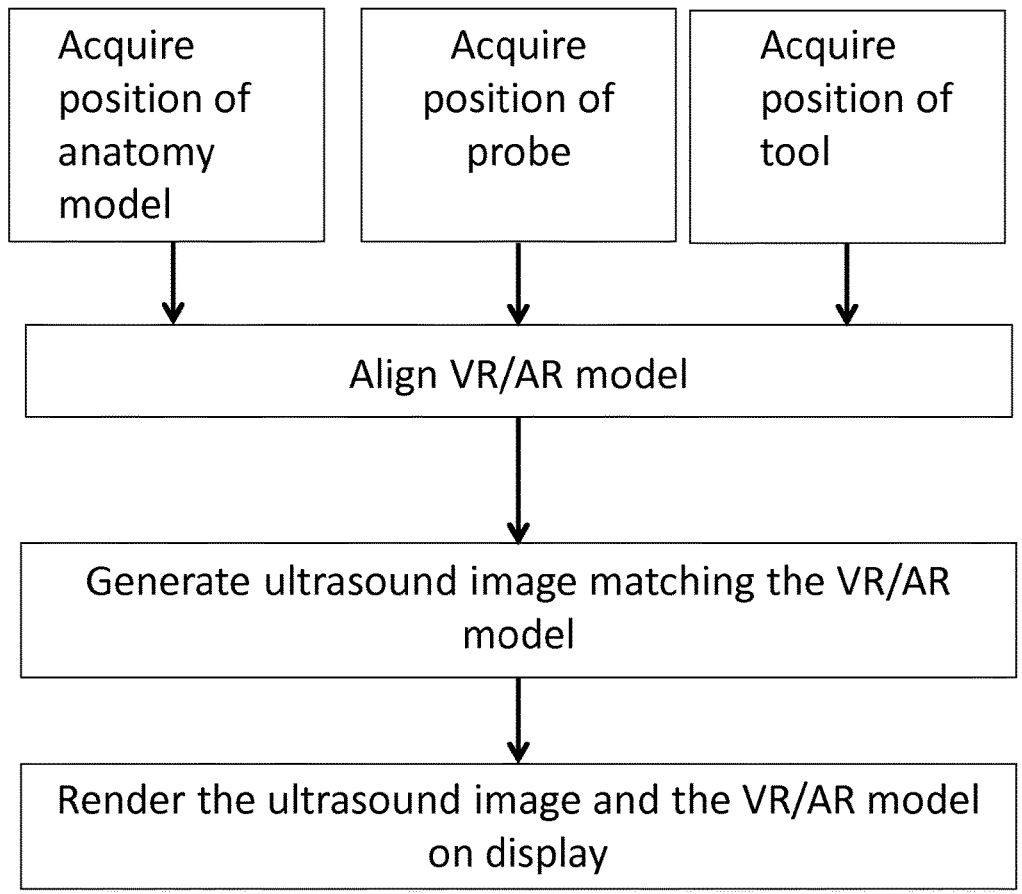
FIG. 7 illustrates a flow chart of an ultrasound simulation method in accordance with different possible embodiments.

FIG. 7 shows a general flowchart of the proposed VR/AR ultrasound simulation method, comprising the steps of:
- Acquiring the position and orientation of the VR/AR simulator elements, such as the anatomy model parts, the ultrasound probe replicate and any medical tools relevant to the ultrasound procedure training;
- Aligning the VR/AR model to the tracked position and orientation of the VR/AR simulator elements;
- Generating an ultrasound image matching the VR/AR model;
- Rendering the ultrasound image and a computer graphics representation of the VR/AR model onto a display screen.

In a possible embodiment, the steps of generating the ultrasound image comprise:
- Interpolating a 2D ultrasound slice by sampling through a standard reconstructed 3D ultrasound volume, as a function of the tracked position and orientation of the VR/AR simulator elements;
- Generating an ultrasound simulation image for additional static VR/AR model elements which do not deform with the ultrasound probe replicate compression, such as the speculum and the catheter tools that are not represented in the reconstructed 3D ultrasound volume, as a function of the tracked position and orientation of the VR/AR simulator elements;
- Blending the 2D ultrasound slice and the ultrasound simulation image into a simulated ultrasound image.

In a possible embodiment, the ultrasound simulation image for the static VR/AR model elements may be represented as a 2D overlay for different tracked position and orientation values of the matching VR/AR simulator elements. In an alternative embodiment, a 3D model may be pre-recorded for the static VR/AR model elements and the ultrasound simulation image may be derived from the 3D model based on the tracked position and orientation of the matching VR/AR simulator elements.

In some embodiments, the interpolation of the 2D ultrasound slice may be adapted as a function of the deformation of the anatomy model 220 due to the pressure of the end user on the ultrasound probe replicate 230 against the anatomy model 220 surface (anatomy model surface compression).

In a possible embodiment, the data processing unit 200 may additionally apply the steps of:
- Measuring a deformation depth as the distance between the ultrasound replicate probe 230 mesh and the anatomy model surface 220 outside mesh (outside mesh corresponding to the anatomy model surface in an initial static position, that is without any deformation applied) in the VR/AR model aligned to the actual position and orientation of the VR/AR simulator elements;
- Interpolating a 2D ultrasound slice by sampling through a standard reconstructed 3D ultrasound volume, as a function of the deformation depth.

Figure 8:
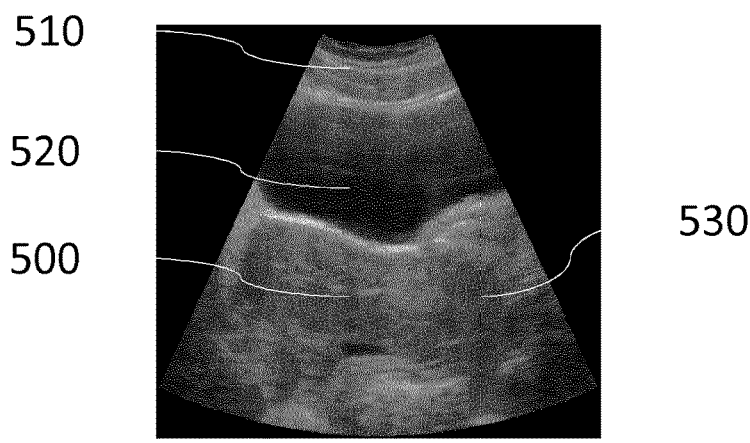
FIG. 8 shows some experimental results of a possible embodiment, where different ultrasound images are rendered for 3 different surface compression levels respectively resulting from (a) low b) medium c) high) ultrasound probe pressure on the anatomy model surface.
Figure 8:
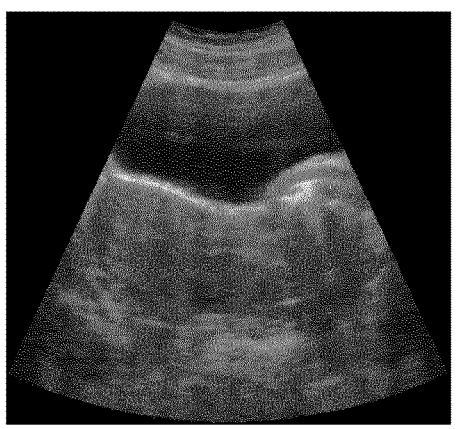
Figure 8:
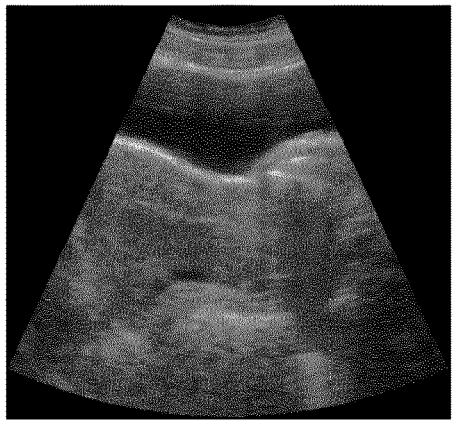

In a possible further embodiment, interpolating a 2D ultrasound slice may comprise: identifying at least one anatomy element to be sampled through a standard reconstructed 3D ultrasound volume, identifying a deformation property for the anatomy element, and interpolating the anatomy element area in the 2D ultrasound slice by sampling through a standard reconstructed 3D ultrasound volume, as a function of the deformation depth and the anatomy element deformation property. FIG. 8 shows some experimental results where different ultrasound images are rendered for 3 different surface compression levels respectively resulting from (a) low b) medium c) high) ultrasound probe replicate 230 compression on the anatomy model 220 surface, with a function of the deformation depth and a predefined stiffness property for the anatomy elements to be interpolated in the 2D ultrasound slice. As visible by comparing the screen captures a), b), c), the abdominal skin 510 layer deforms moderately (moderate stiffness), the moderately filled bladder 520 deforms a lot (low stiffness) while the uterine cavity (high stiffness) does not significantly deform under the pressure of the ultrasound probe replicate 230 pressure on the anatomy model 220 surface. As will be apparent to those skilled in the art, modeling tissue compression as a function of depth for different anatomy elements, for instance in FIG. 8 the skin, the bladder and the uterine elements, is a low-complexity alternative to a more formal physics simulation methods such as finite-element methods (FEM), thus having positive impact on scene setup complexity and simulator performance, while maintaining a high level of realism.

In a possible embodiment, the ultrasound simulation overlay image modeling step for additional VR/AR model elements takes into account the VR/AR model physical properties, for instance a metal tool such as the speculum 240 may cast some shield shadows 530 in the ultrasound image according to its relative position to the ultrasound probe replicate 230.

Figure 9:
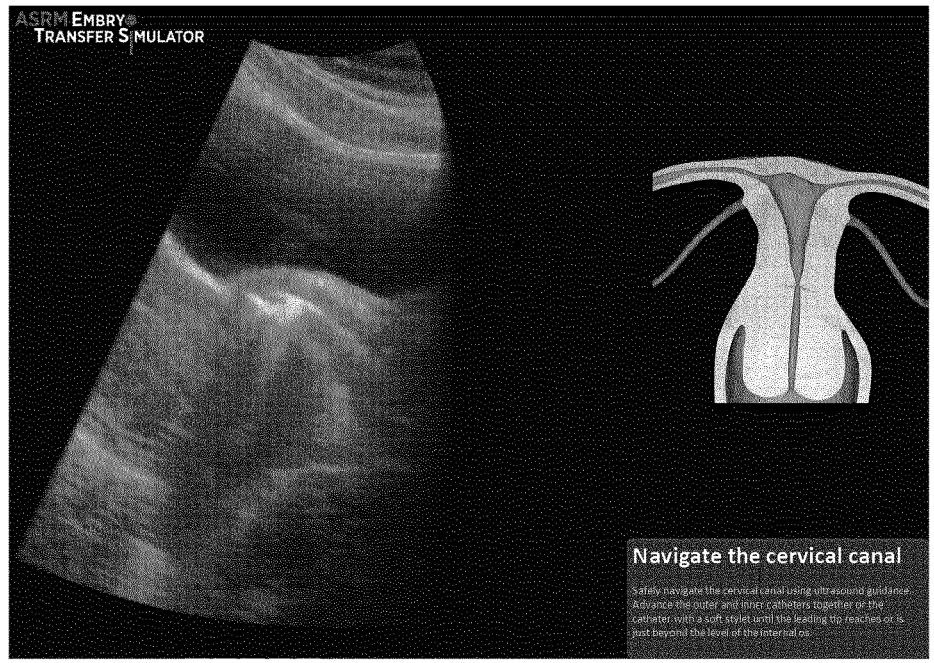
FIG. 9 shows a screen capture of an abdominal ultrasound simulation where the ultrasound probe replicate has been tilted on the left or the right at the boundary of the ultrasound possible capture.
Figure 9:
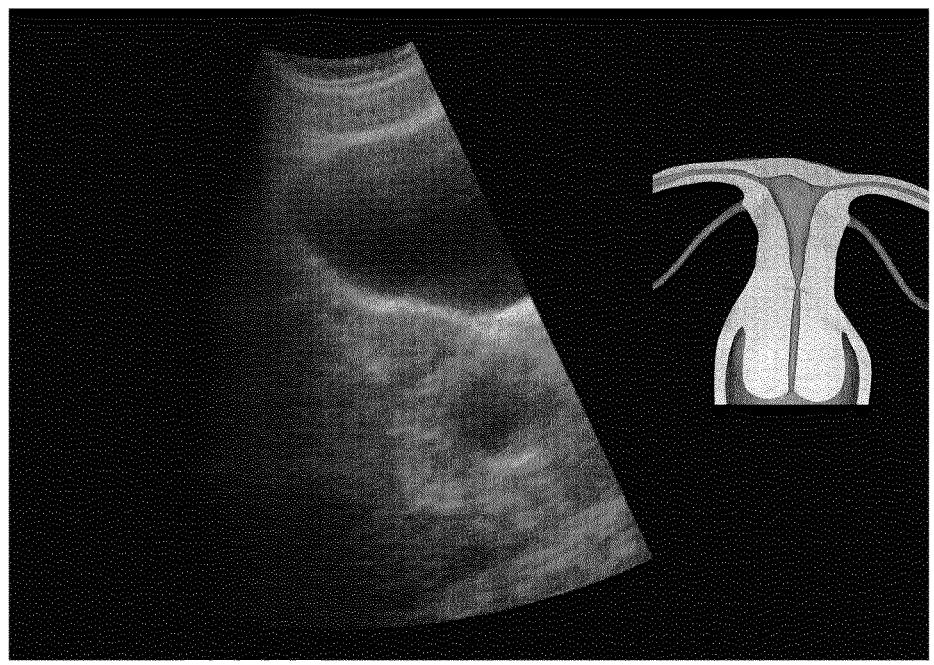
Figure 10:
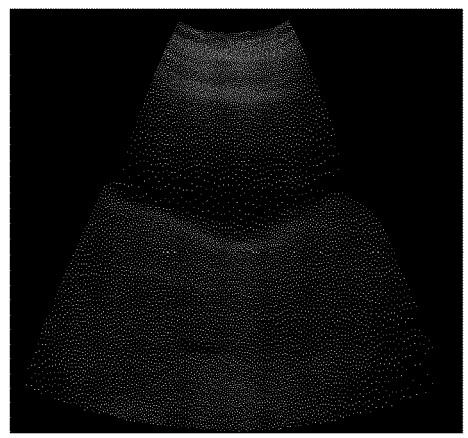
FIG. 10 shows a screen capture of an abdominal ultrasound simulation rendering for various compression levels of the ultrasound probe replicate on the anatomy model surface.
Figure 10:
Figure 10:
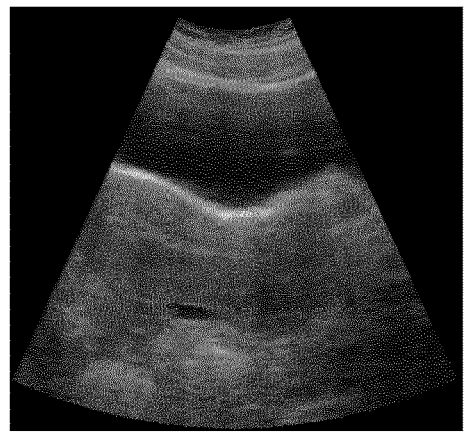

In some embodiments, the trainee may translate the ultrasound probe replicate position over the curved surface of the anatomy model 220, lift the ultrasound probe replicate out of contact with the anatomy model 220 surface, and/or tilt the ultrasound probe replicate orientation out of a realistic field of view area. The ultrasound image field of view may therefore be adapted to depend on the actual position and orientation of the ultrasound probe replicate relative to the model for a more realistic ultrasound training experience. In a possible further embodiment, the ultrasound image may be faded out in accordance with the actual tilting of the ultrasound probe replicate, or when the 3D volume data edge is reached, as illustrated for instance by FIG. 9*a*) (right tilt) and *b*) (left tilt). Fading may consist in progressively replacing the image with a black image or with a noisy image corresponding to typical ultrasound imaging noise. The tool shield shade placement may be adapted accordingly, as visible for instance on FIG. 8*a*). FIG. 10) shows further fade-out rendering of three different user interaction with the ultrasound replicate probe 230 over the anatomy model 220 surface when simulating an abdominal ultrasound capture: *a*) simple contact of the probe with the anatomy model surface, without any pressure or deformation, which prevents a good ultrasound capture in medical practice, thus a very dark and/or blurred image; *b*) little pressure by the probe over the anatomy model surface, which slightly improves the image; *c*) regular pressure by the probe over the anatomy model surface, which results in a satisfactory ultrasound image as expected in abdominal ultrasound practice.

In some embodiments, the medical tool 240 is made of a material, such as metal, which acts as a shield to ultrasound waves. The tool shield thus cast its shadow accordingly on the ultrasound image, depending on the actual position and orientation of the ultrasound probe replicate relative to the tool. In a possible further embodiment (not illustrated), the tool, for instance the speculum, may also be moved by the user during the training procedure. Thanks to accurate tracking of both the ultrasound probe replicate, the anatomy model and the tool with position and orientation sensors, the simulation system and method may accurately detect the actual simulator configuration and adapt the rendering accordingly.

The methods and systems disclosed herein may be further adapted to a number of other ultrasound training scenarios. For instance the anatomy model 220 surface may be further deformed from additional user interaction with another tool or the user hand (for instance pressing on the belly with the other hand). The anatomy model may also be further deformed by breathing. While the present disclosure primarily described an abdominal ultrasound examination such as the one applied in the embryo transfer procedure, other ultrasound examination procedures may be simulated, such as for instance a transvaginal ultrasound examination in routine gynecology practice.

As will be apparent to those skilled in the art of medical ultrasound imaging, registered ultrasound volumes may have a limited field-of-view (FOV) which restricts the use of 3D ultrasound data to imaging of small or only parts of organs and structures. Prior art models with a limited FOV do not allow for freely exploring the full anatomy, which may be important when diagnosing patients later on. For instance in a number of OBGYN ultrasound imaging simulation scenarios, the underlying volume needs to cover for example the full abdomen to provide a realistic setting for training the end user. Extending the FOV may be achieved by stitching several of the small volumes together to one large volume, which may be pre-computed and recorded as a single reference volume. Alternately, several 3D ultrasound volumes may be attached to the tracked position and orientation of certain anatomy model elements, for instance the cervix in an OBGYN examination simulation, to cover a broader field of view than each ultrasound volume covers individually, and the 2D ultrasound slice may be interpolated by sampling through the combined and deformed ultrasound volumes.

In some ultrasound applications, deformation may also be induced by heart beating or digestive tract muscle motion. While in the present disclosure, a simple deformation model based on the compression depth measurement and predefined stiffness of the anatomy elements has been described, various alternate deformation models may be used, such as for instance the Finite Element Methods (FEM) as proposed by Goksel et al.

While a VR/AR ultrasound simulator for the IVF embryo transfer procedure has been detailed herein as an example for a better illustration of the disclosure, the proposed methods and systems can be generalized to any type of ultrasound simulations.

While a passive haptic VR/AR ultrasound simulator has been detailed herein as an example for a better illustration of the disclosure, the proposed methods and systems can be generalized to any type of hardware simulator setups. In particular, various position and orientation tracking means may be used, such as magnetic or optical tracking systems, or a mix of such systems. Various calibration procedures may also be used. Active haptic hardware may also be integrated into the VR/AR ultrasound simulator.

While a VR/AR ultrasound simulation method using interpolation from a reconstructed 3D ultrasound volume has been detailed herein as an example for a better illustration of the disclosure, the proposed methods and systems can be generalized to any type of ultrasound imaging simulations. In particular, generative ray-based simulation systems and methods may also be used for ultrasound image modeling.

While various embodiments of an IVF embryo transfer simulator have been described above, it should be understood that they have been presented by way of example and not limitation. It will be apparent to persons skilled in the relevant art(s) that the proposed methods and systems can be generalized to any type of ultrasound simulations. Various changes in form and detail can be made therein without departing from the spirit and scope. In fact, after reading the above description, it will be apparent to one skilled in the relevant art(s) how to implement alternative embodiments. Thus, the present embodiments should not be limited by any of the above-described embodiments.

In addition, it should be understood that any figures which highlight the functionality and advantages are presented for example purposes only. The disclosed methodology and system are each sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

The invention claimed is:

1. An ultrasound simulation method for rendering on a display an ultrasound image of an anatomy model, the method comprising:

acquiring, with at least one anatomy model sensor, a position and orientation of an anatomy model;

acquiring, with at least one probe replicate sensor, a position and orientation of an ultrasound imaging probe replicate, the ultrasound imaging probe replicate being adapted to interact with low friction with at least one deformable anatomy model surface without requiring the use of ultrasound gel, the anatomy model surface being deformed under the pressure of the ultrasound imaging probe replicate;

aligning a virtual reality/augmented reality (VR/AR) model to the acquired position and orientation of the anatomy model and of the ultrasound imaging probe replicate;

measuring a deformation depth as the distance between the ultrasound imaging probe replicate surface position and the initial anatomy model surface position before anatomy model surface deformation;

identifying at least one anatomy element in a two dimensional (2D) ultrasound slice to be sampled through a standard reconstructed three dimensional (3D) ultrasound volume;

identifying a deformation property for the anatomy element;

interpolating the anatomy element area in the 2D ultrasound slice by sampling through a standard reconstructed 3D ultrasound volume, as a function of the measured deformation depth and the identified anatomy element deformation property;

rendering on a display the 2D ultrasound slice comprising the interpolated anatomy element.

2. The method of claim 1, wherein the deformation property for the anatomy element is pre-defined stiffness parameter.

3. The method of claim 2, wherein interpolating a 2D ultrasound slice further comprises: attaching at least two 3D ultrasound volumes to the tracked position and orientation of the anatomy model and interpolating a 2D ultrasound slice by sampling through the combined ultrasound as a function of the tracked position and orientation of the anatomy model and the probe replicate.

4. The method of claim 2, wherein interpolating a 2D ultrasound slice further comprises: attaching at least two 3D ultrasound volumes to the tracked position and orientation of the anatomy model and interpolating a 2D ultrasound slice by sampling through the combined 3D ultrasound volumes as a function of the deformation depth.

5. The method of claim 2, further comprising:
acquiring a position and orientation of a tool which does not deform with the ultrasound probe compression;
aligning a VR/AR model to the acquired position and orientation of the anatomy model, of the ultrasound imaging probe replicate and of the tool;
generating an ultrasound simulation image for static VR/AR model elements of the tool which do not deform with the ultrasound probe replicate compression, that are not represented in the reconstructed 3D ultrasound volume, as a function of the tracked position and orientation of the VR/AR simulator elements;
blending the 2D ultrasound slice and the ultrasound simulation image for static VR/AR model elements into a blended ultrasound image;
rendering the blended ultrasound image onto a display.

6. The method of claim 1, wherein interpolating a 2D ultrasound slice further comprises: attaching at least two 3D ultrasound volumes to the tracked position and orientation of the anatomy model and interpolating a 2D ultrasound slice by sampling through the combined ultrasound as a function of the tracked position and orientation of the anatomy model and the probe replicate.

7. The method of claim 6, wherein interpolating a 2D ultrasound slice further comprises: attaching at least two 3D ultrasound volumes to the tracked position and orientation of the anatomy model and interpolating a 2D ultrasound slice by sampling through the combined 3D ultrasound volumes as a function of the deformation depth.

8. The method of claim 6, further comprising:
acquiring a position and orientation of a tool which does not deform with the ultrasound probe compression;
aligning a VR/AR model to the acquired position and orientation of the anatomy model, of the ultrasound imaging probe replicate and of the tool;
generating an ultrasound simulation image for static VR/AR model elements of the tool which do not deform with the ultrasound probe replicate compression, that are not represented in the reconstructed 3D ultrasound volume, as a function of the tracked position and orientation of the VR/AR simulator elements;
blending the 2D ultrasound slice and the ultrasound simulation image for static VR/AR model elements into a blended ultrasound image;
rendering the blended ultrasound image onto a display.

9. The method of claim 1, wherein interpolating a 2D ultrasound slice further comprises: attaching at least two 3D ultrasound volumes to the tracked position and orientation of the anatomy model and interpolating a 2D ultrasound slice by sampling through the combined 3D ultrasound volumes as a function of the deformation depth.

10. The method of claim 9, further comprising:
acquiring a position and orientation of a tool which does not deform with the ultrasound probe compression;
aligning a VR/AR model to the acquired position and orientation of the anatomy model, of the ultrasound imaging probe replicate and of the tool;
generating an ultrasound simulation image for static VR/AR model elements of the tool which do not deform with the ultrasound probe replicate compression, that are not represented in the reconstructed 3D ultrasound volume, as a function of the tracked position and orientation of the VR/AR simulator elements;
blending the 2D ultrasound slice and the ultrasound simulation image for static VR/AR model elements into a blended ultrasound image;
rendering the blended ultrasound image onto a display.

11. The method of claim 1, further comprising:
acquiring a position and orientation of a tool which does not deform with the ultrasound probe compression;
aligning a VR/AR model to the acquired position and orientation of the anatomy model, of the ultrasound imaging probe replicate and of the tool;
generating an ultrasound simulation image for static VR/AR model elements of the tool which do not deform with the ultrasound probe replicate compression, that are not represented in the reconstructed 3D ultrasound volume, as a function of the tracked position and orientation of the VR/AR simulator elements;
blending the 2D ultrasound slice and the ultrasound simulation image for static VR/AR model elements into a blended ultrasound image;
rendering the blended ultrasound image onto a display.

12. The method of claim 11, wherein the position and orientation of a tool is acquired with a position and orientation sensor.

13. The method of claim 12, wherein the ultrasound simulation image for the static VR/AR model elements not represented in the reconstructed 3D ultrasound volume is a 2D overlay image.

14. The method of claim 12, wherein the ultrasound simulation image for additional VR/AR model elements not represented in the reconstructed 3D ultrasound volume is derived from a pre-recorded 3D model.

15. The method of claim 11, wherein the tool is fixed to an anatomy model element and the tool position and orientation of the tool is derived from the anatomy model position and orientation.

16. The method of claim 15, wherein the ultrasound simulation image for the static VR/AR model elements not represented in the reconstructed 3D ultrasound volume is a 2D overlay image.

17. The method of claim 11, wherein the ultrasound simulation image for the static VR/AR model elements not represented in the reconstructed 3D ultrasound volume is a 2D overlay image.

18. The method of claim 11, further comprising:
calculating a fading of a simulated ultrasound image as a function of the tracked position and orientation of the anatomy model and the ultrasound probe replicate;
rendering the faded simulated ultrasound image onto a display.

19. The method of claim 11, wherein the ultrasound simulation image for additional VR/AR model elements not represented in the reconstructed 3D ultrasound volume is derived from a pre-recorded 3D model.

20. The method of claim 11, wherein the tool is made of metal and casts shield shadows in the ultrasound simulation image according to its relative position to the ultrasound probe replicate.

* * * * *